(12) United States Patent
Chapman et al.

(10) Patent No.: US 10,490,308 B2
(45) Date of Patent: *Nov. 26, 2019

(54) CONTEXT-SENSITIVE CHEST COMPRESSION FRACTION MEASUREMENT FOR CPR QUALITY ASSESSMENT

(71) Applicant: Physio-Control, Inc., Redmond, WA (US)

(72) Inventors: Fred W. Chapman, Newcastle, WA (US); Robert G. Walker, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 482 days.

This patent is subject to a terminal disclaimer.

(21) Appl. No.: 14/069,112

(22) Filed: Oct. 31, 2013

(65) Prior Publication Data

US 2014/0188500 A1 Jul. 3, 2014

Related U.S. Application Data

(60) Provisional application No. 61/767,141, filed on Feb. 20, 2013.

(51) Int. Cl.
*G16H 50/30* (2018.01)
*A61N 1/39* (2006.01)
(Continued)

(52) U.S. Cl.
CPC .......... *G16H 50/30* (2018.01); *A61B 5/0245* (2013.01); *A61H 31/005* (2013.01); *A61N 1/39* (2013.01); *A61N 1/39044* (2017.08)

(58) Field of Classification Search
CPC ..... A61B 5/0205; A61B 5/046; A61B 5/0809; A61B 5/024; G06Q 50/22; G06Q 50/24
See application file for complete search history.

(56) References Cited

U.S. PATENT DOCUMENTS 4,060,079 A 11/1977 Reinhold
4,237,872 A 12/1980 Harrigan et al.
(Continued)

FOREIGN PATENT DOCUMENTS

EP 1057451 12/2000
EP 1859770 11/2007
(Continued)

OTHER PUBLICATIONS

International Search Report & Written Opinion by PCT Authority for PCT/US2014/017213, dated May 9, 2014.
(Continued)

*Primary Examiner* — Elaine Gort
*Assistant Examiner* — Rachelle L Reichert
(74) *Attorney, Agent, or Firm* — Lane Powell PC (57) ABSTRACT

Devices, systems, software and methods for CPR quality assessment. Patient data is received that may be derived from a session of administering sets of CPR chest compressions to a patient. The sets can be separated by pauses. Then a figure of merit (FOM) can be computed from the data. In the computation, at least one pause can contribute a penalty to the FOM. The penalty has a value determined from at least one control factor, other than a constant linear dependence on the duration of the pause. This way, pauses can incur penalties to the FOM computation depending on their context, instead of merely their duration. For example, a penalty can escalate non-linearly if its pause becomes unduly long, or if it follows a set of chest compressions that was unduly short. As such, a better CPR quality assessment is achieved.

18 Claims, 7 Drawing Sheets

(51) Int. Cl.
*A61B 5/0245* (2006.01)
*A61H 31/00* (2006.01)
*C07D 413/14* (2006.01)

(56) References Cited

U.S. PATENT DOCUMENTS

| | | |
|---|---|---|
| 4,397,306 A | 8/1983 | Weisfeldt et al. |
| 4,424,806 A | 1/1984 | Newman et al. |
| 4,570,615 A | 2/1986 | Barkalow et al. |
| 4,610,254 A | 9/1986 | Morgan et al. |
| 4,797,104 A | 1/1989 | Laerdal et al. |
| 4,928,674 A | 5/1990 | Halperin et al. |
| 5,020,516 A | 6/1991 | Biondi et al. |
| 5,077,667 A | 12/1991 | Brown et al. |
| 5,261,394 A | 11/1993 | Mulligan et al. |
| 5,334,070 A | 8/1994 | Yu et al. |
| 5,490,820 A | 2/1996 | Schock et al. |
| 5,716,318 A | 2/1998 | Manning et al. |
| 5,722,613 A | 3/1998 | Michael et al. |
| 5,743,864 A | 4/1998 | Baldwin et al. |
| 5,749,902 A | 5/1998 | Olson et al. |
| 5,997,488 A | 12/1999 | Gelfand et al. |
| 6,125,299 A | 9/2000 | Groenke et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,390,996 B1 | 5/2002 | Halperin et al. |
| 6,398,745 B1 | 6/2002 | Sherman et al. |
| 6,438,419 B1 | 8/2002 | Callaway et al. |
| 6,676,613 B2 | 1/2004 | Cantrell et al. |
| 6,697,671 B1 | 2/2004 | Myklebust et al. |
| 6,827,695 B2 | 12/2004 | Palazzolo et al. |
| 7,272,441 B1 | 9/2007 | Chapman et al. |
| 7,311,680 B2 | 12/2007 | Lenhart et al. |
| 7,630,762 B2 | 12/2009 | Sullivan et al. |
| 7,717,855 B2 | 5/2010 | Caldarone et al. |
| 7,805,191 B2 | 9/2010 | Walker et al. |
| 8,060,199 B2 | 11/2011 | Walker et al. |
| 8,135,460 B2 | 3/2012 | Sullivan et al. |
| 8,343,081 B2 | 1/2013 | Walker et al. |
| 8,433,407 B2 | 4/2013 | Chapman et al. |
| 8,795,208 B2 | 8/2014 | Walker et al. |
| 8,942,800 B2 | 1/2015 | Thiagrajan et al. |
| 9,126,055 B2 | 9/2015 | Abdeen et al. |
| 2002/0117173 A1 | 8/2002 | Lynn et al. |
| 2002/0133197 A1 | 9/2002 | Snyder et al. |
| 2003/0135085 A1 | 7/2003 | Bassuk et al. |
| 2003/0135139 A1 | 7/2003 | Bassuk et al. |
| 2003/0195775 A1 | 10/2003 | Hampton et al. |
| 2004/0082888 A1 | 4/2004 | Palazzolo et al. |
| 2004/0225238 A1 | 11/2004 | Sherman et al. |
| 2004/0230140 A1 | 11/2004 | Steen et al. |
| 2005/0165335 A1 | 7/2005 | Sherman et al. |
| 2006/0089574 A1 | 4/2006 | Paradis et al. |
| 2006/0111749 A1 | 5/2006 | Westenskow et al. |
| 2006/0173500 A1* | 8/2006 | Walker et al. ............ 607/5 |
| 2006/0173501 A1* | 8/2006 | Stickney et al. ............ 607/5 |
| 2007/0004992 A1 | 1/2007 | Van Brunt et al. |
| 2008/0146974 A1 | 6/2008 | Lind et al. |
| 2009/0270930 A1 | 10/2009 | Walker et al. |
| 2010/0016910 A1 | 1/2010 | Sullivan et al. |
| 2010/0022904 A1 | 1/2010 | Centen |
| 2010/0152800 A1* | 6/2010 | Walker et al. ............ 607/5 |
| 2011/0082510 A1 | 4/2011 | Sullivan et al. |
| 2011/0297147 A1 | 12/2011 | Lick et al. |
| 2012/0010543 A1* | 1/2012 | Johnson et al. ............ 601/41 |
| 2012/0123224 A1 | 5/2012 | Packer et al. |
| 2012/0136286 A1 | 5/2012 | Nova et al. |
| 2013/0023781 A1 | 1/2013 | Freeman et al. |
| 2013/0282069 A1* | 10/2013 | Thiagarajan et al. ............ 607/3 |

FOREIGN PATENT DOCUMENTS

| | | |
|---|---|---|
| EP | 1933114 | 6/2008 |
| EP | 2446124 | 6/2008 |
| WO | 1999024114 | 5/1999 |
| WO | 2004037154 | 5/2004 |
| WO | 2007033050 | 3/2007 |

OTHER PUBLICATIONS

International Search Report and Written Opinion by PCT Authority for PCT/US2014/017213 dated May 9, 2014.
Walker R. Brouwer T, Chapman F, Koster R. Lack of correlation between chest compression fractions over 0.4 and survival. Prehospital Emergency Care 2013; 17(1):118,A62. Abstract.
Brouwer T. Walker R, Chapman F, Koster R. Duration of longest chest compression interruption predicts poor cardiac arrest survival independent of chest compression fraction. Circulation 2012;126:A87. Abstract.
Berg RA, et al., Part 5: adult basic life support: 2010 American Heart Association Guidelines for Cardiopulmonary Resuscitation and Emergency Cardiovascular Care. Circulation. Nov. 2, 2010; 122 (18 Suppl 3); S685-705.
Dave DM, et al., Part 7: CPR techniques and devices: 2010 American Heart Association Guidelines for Cardiopulmonary Resuscitation and Emergency Cardiovascular Care. Circulation. Nov. 2, 2010; 122(18 Suppl 3): S720-8.
Chapman, F.W., et al., "A Feedback Controller for Ventilatory Therapy", Annals of Biomedical Engineering, 1985, 13, 359-372.
Cobb, Leonard A., Changing Incidence of Out-of-Hospital Ventricular Fibrillation, 1980-2000, JAMA, Dec. 18, 2002, p. 3008-3013, vol. 288, No. 23.
Diaz, et al., "Modifying the first minute of reperfusion: potential for myocardial salvage", Cardiovascular Research 62, 2004 p. 4-6 Elsevier B.V.
Galagudza et al., "Ischemic postconditioning: brief ischemia during reperfusion converts persistent ventricular fibrillation into regular rhythm", European Journal of Cardiothoracic Surgery, 25, (2004) p. 1006-1010 Elsevier B.V.
Halkos et al., The Society of Thoracic Surgeons, 2004, p. 961-969, Elsevier Inc.
Hallstrom et al., "Cardiopulmonary Resuscitation by Chest Compression Alone or with Mouth-To-Mouth Ventilation", May 25, 2000, The New England Journal of Medicine, vol. 342, No. 21, pp. 1546-1553.
Heusch, "Postconditioning, Old Wine in a New Bottle?" Journal of the American College of Cardiology, 2004, vol. 44, No. 5, p. 1111-1112, Elsevier Inc.
International Search Report and Written Opinion, PCT/US2005/39633, Intl. filed Nov. 2, 2005, 4 pages.
Kern et al., "Efficacy of Chest Compression-Only BLS CPR in the Presence of an Occluded Airway", 1998, Elsevier Science Ireland Ltd., Resuscitation 39 (1998), Accepted Nov. 11, 1998, pp. 179-188.
Kin et al., "Postconditioning attenuates myocardial ischemia-reperfusion injury by inhibiting events in the early minutes of reperfusion", Cardiovascular Research 62, 2004, p. 75-85, Elsevier B.V.
Maquet Servo Ventilator 900 C/D/E, Service Manual, Maquet Critical Care AB, May 2009, 55 pages.
Neumar RW, et al., Part 8: Adult advanced cardiovascular life support: 2010 American Heart Association Guidelines for Cardiopulmonary Resuscitation and Emergency Cardiovascular Care. Circulation. Nov. 2, 2010: 122(18 Suppl 3): S729-67.
Ovize M, et al., "Working Group of Cellular Biology of Heart of European Society of Cardiology. Postconditioning and protection from reperfusion injury: where do we stand?" Position paper from the Working Group of Cellular Biology of the Heart of the European Society of Cardiology. Cardiovasc Res. Aug. 1, 2010; 87(3):406-423.
Part 4: Adult Basic Life Support, Circulation, 2005, 112: IV-18 to IV-34.
Part 6: CPR Techniques and Devices, Circulation, 2005, 112: IV-47 to IV-50.
Responsive Amendment dated Jul. 1, 2009 for U.S. Appl. No. 11/961,687 (13 pgs.).

(56) References Cited

OTHER PUBLICATIONS

Segal N, et al., "Ischemic postconditioning at the initiation of cardiopulmonary resuscitation facilitates functional cardiac and cerebral recovery after prolonged untreated ventricular fibrillation", Resuscitation. Nov. 2012; 83(11):1397-1403.

Travers AH, et al., Part 4: CPR overview: 2010 American Heart Association Guidelines for Cardiopulmonary Resuscitation and Emergency Cardiovascular Care. Circulation. Nov. 2, 2010; 122 (18 Suppl 3):5676-5684.

Tsang et al., "Postconditioning: A Form of Modified Reperfusion Protects the Myocardium by Activating the Phosphatidylinositol 3-Kinase-Akt Pathway", Circulation Research, 2004 p. 230-232 American Heart Association Inc.

U.S. Appl. No. 11/272,177, filed Nov. 10, 2005, CPR Performance Reporting Systems.

Wang JY, et al., "Ischemic postconditioning protects against global cerebral ischemia/reperfusion-induced injury in rats", Stroke. Mar. 2008; 39(3):983-990.

Weisfeldt, Resuscitation After Cardiac Arrest, JAMA, Dec. 18, 2002, p. 3035-3038, vol. 288, No. 23.

Wik, Lars, Delaying Defibrillation to Give Basic Cardopulmonary Resuscitation to Patients With Out-of-Hospital Ventricular Fibrillation, JAMA, Mar. 19, 2003, p. 1389-1395, vol. 289, No. 11.

Wik, Lars, MD, PhD, Quality of Cardiopulmonary Resuscitation During Out-of-Hospital Cardiac Arrest, (Reprinted) JAMA, Jan. 19, 2005—vol. 293, No. 3, pp. 299-304.

Yang, et al., "Multiple, Brief Coronary Occlusions During Early Reperfusion Protect Rabbit Hearts by Targeting Cell Signaling Pathways", Journal of the American College of Cardiology, 2004 vol. 44 No. 5 PO 1103-1110 Elsevier Inc.

Yannopoulos D, et al., "Controlled pauses at the initiation of sodium nitroprusside-enhanced cardiopulmonary resuscitation facilitate neurological and cardiac recovery after 15 mins of untreated ventricular fibrillation", Crit Care Med May 2012; 40(5):1562-1569.

Yannopoulos D, et al., "Ischemic post-conditioning and vasodilator therapy during standard cardiopulmonary resuscitation to reduce cardiac and brain injury after prolonged untreated ventricular fibrillation", Resuscitation. Aug. 2013; 84(8):1143-9. Epub Jan. 29, 2013.

Zhao, et al., "Inhibition of myocardial injury by ischemic postconditioning during reperfusion: comparison with ischemic preconditioning". Am J. Physiol Heart Circ Physiol 285, 2003, p. H579-H588 The American Physiological Society.

Zhao, Heng, "The Protective Effects of Ischemic Postconditioning against Stroke: From Rapid to Delayed and Remote Postconditioning", The Open Drug Discovery Journal, 2010, 2, 138-147.

Zhou Y, et al., "Postconditioning in cardiopulmonary resuscitation: a better protocol for cardiopulmonary resuscitation", Med Hypotheses, Sep. 2009; 73(3):321-323. 2009.03.014. Epub Apr. 24, 2009.

Zoll Data Systems, "RescueNet Code Review, Getting Started Guide-Version 5.20", dated Aug. 25, 2005.

International Preliminary Report on Patentability dated Aug. 25, 2015, by PCT Authority for PCT/US2014/017213 International filed Feb. 19, 2014.

* cited by examiner

FIG. 1

FIG. 2  *DEFIBRILLATION SCENE*

FIG. 5  *COMPUTING THE FIGURE OF MERIT*

*COMPUTATION OF PAUSE PENALTIES*

FIG. 6 (PRIOR ART)

FIG. 7  *COMPUTATION OF PAUSE PENALTIES*

FIG. 8  *COMPUTATION OF PAUSE PENALTIES*

FIG. 9  COMPUTATION OF PAUSE PENALTIES

FIG. 10  COMPUTATION OF PAUSE PENALTIES

*METHODS*

FIG. 11

CONTEXT-SENSITIVE CHEST COMPRESSION FRACTION MEASUREMENT FOR CPR QUALITY ASSESSMENT

CROSS REFERENCE TO RELATED PATENT APPLICATIONS

This patent application claims priority from U.S. Provisional Patent Application Ser. No. 61/767,141 filed on Feb. 20, 2013, titled: "A CONTEXT-SENSITIVE CHEST COMPRESSION FRACTION MEASUREMENT FOR CPR QUALITY ASSESSMENT", the disclosure of which is hereby incorporated by reference for all purposes.

BACKGROUND

In humans, the heart beats to sustain life. In normal operation, the heart pumps blood through the various parts of the body. Sometimes the heart malfunctions, in which case it can beat irregularly, or not at all. The cardiac rhythm is then generally called an arrhythmia. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively and, if not treated, death can occur. In fact, it is estimated that SCA results in more than 250,000 deaths per year in the United States alone. Further, a SCA may result from a condition other than an arrhythmia. One type of arrhythmia associated with SCA is known as Ventricular Fibrillation (VF). VF is a type of heart malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes, the rate of survival for SCA victims averages less than 2%.

During VF, the person's condition deteriorates, because blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

CPR chest compressions must be administered continuously. Methods have been devised for assessing a rescue team's performance, so as to help them improve their training. A method by Physio-Control, Inc. is described in U.S. Pat. No. 8,060,199 B2, which is hereby incorporated by reference. One or more figures of merit are computed about the administered CPR.

BRIEF SUMMARY

The present description gives instances of devices, systems, software, and methods for CPR quality assessment, the use of which may help overcome problems and limitations of the prior art In one embodiment, patient data is received. The patient data may be derived from a session of administering sets of CPR chest compressions to a patient. The sets can be separated by pauses. Then a figure of merit (FOM) can be computed from the data. In the computation, at least one pause can contribute a penalty to the FOM. The penalty has a value determined from at least one control factor, other than a constant linear dependence on the duration of the pause.

An advantage over the prior art is that pauses can incur penalties to the FOM computation depending on their context, instead of merely their duration. For example, a penalty can escalate non-linearly if its pause becomes unduly long, or if it follows a set of chest compressions that was unduly short. As such, a better CPR quality assessment is achieved.

These and other features and advantages of this description will become more readily apparent from the following Detailed Description, which proceeds with reference to the drawings, in which:

DETAILED DESCRIPTION

As has been mentioned, the present description is about devices, systems, software, and methods for computing a Figure of Merit (FOM). Embodiments are now described in more detail.

Figure 1:
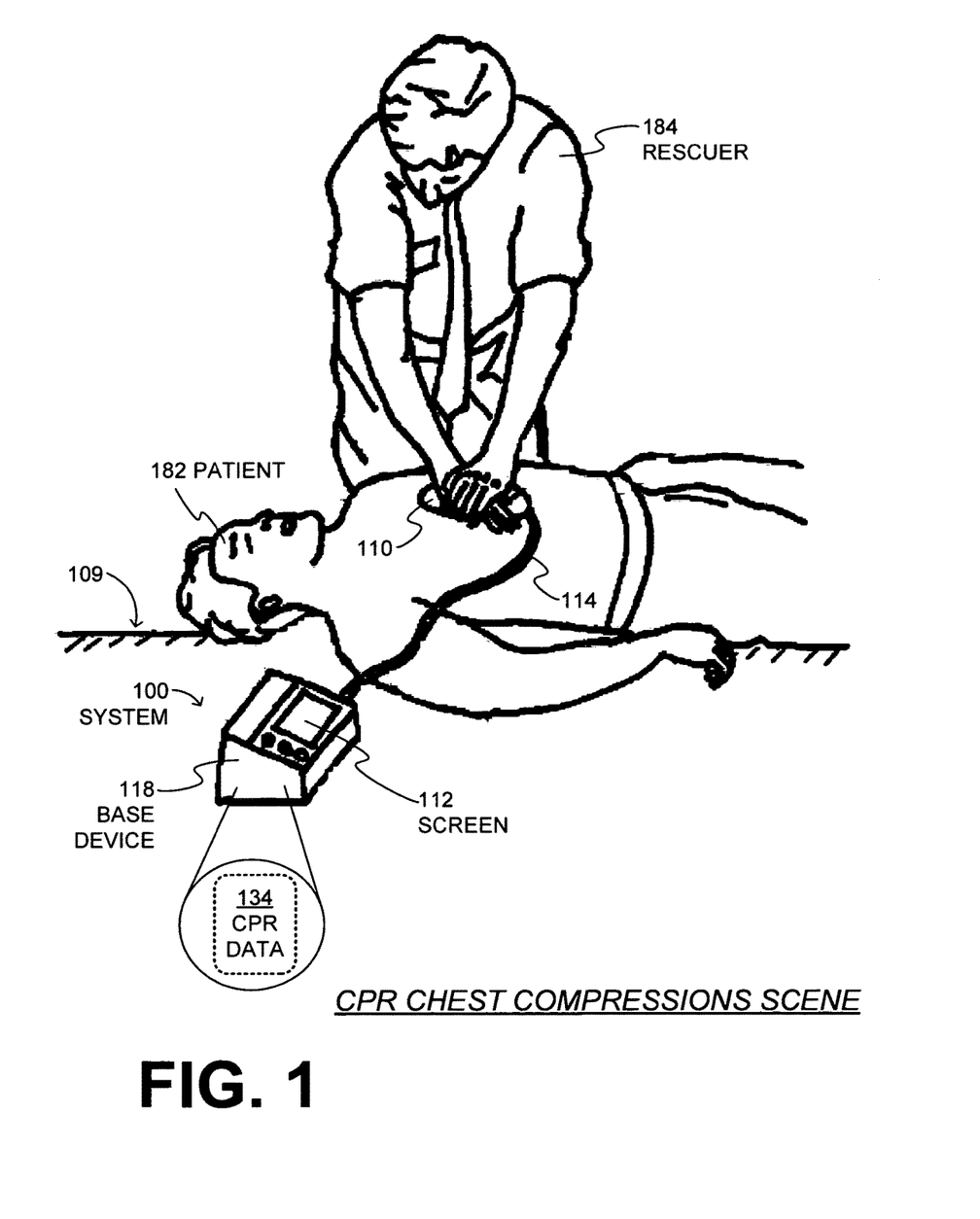
FIG. 1 is a diagram of a scene where a rescuer is performing chest compressions on a patient using a CPR feedback apparatus according to embodiments.

FIG. 1 is a diagram of a scene where a rescuer 184 is performing chest compressions on a patient 182 who is lying on ground 109. Rescuer 184 is also using a sample system 100 which is made according to embodiments. Particular system 100 is for CPR feedback only, but that need not be the case according to embodiments.

System 100 includes a sensor 110 that is configured to be placed on as patient's chest. Sensor 110 is configured to detect a time displacement of the chest of patient 182, as patient 182 is receiving CPR chest compressions. More particularly, patient 182 is receiving sets of CPR chest compressions that are separated by pauses. Sensor 110 can be made in any way known in the art for CPR feedback devices.

System 100 also includes a base device 118. Base device 118 has a user interface. User interface may be implemented in any way known in the art for being used by rescuer 184. In the example of FIG. 1, the user interface includes a screen 112. Base device 118 may be operatively coupled to input from sensor 110 patient data from the detected time displacement of the chest. In the example of FIG. 1, coupling is by wire 114, although coupling may be wireless, such as magnetic, electromagnetic, and so on. The inputted patient data is shown in the example of FIG. 1 as CPR data 134 within base device 118. Of course, this CPR data reflects the above-mentioned sets of CPR chest compressions that are separated by pauses.

As mentioned above, the system need not be dedicated to being only a CPR feedback system, such as system 100. Rather, the system could be part of a monitor-defibrillator, in which case the base device has correspondingly additional capabilities. For example, the base device could include a defibrillation module, configured to defibrillate the patient, if need be.

System 100 further includes a processor, which is not shown in FIG. 1. It is preferred that the processor is within base device 118. The processor can be configured to compute a Figure of Merit (FOM) for the CPR chest compressions according to embodiments. Examples of computations are described in more detail later in this document.

The user interface of the system can be configured to output a value of the FOM. In the example of FIG. 1, screen 112 of system 100 can display the value. The user interface is preferably also configured to output an alarm, if the value of the FOM exceeds a threshold. For example, the user interface can also include a speaker, a beeper, a light, and so on. The alarm would be superfluous, if it could be guaranteed that rescuer 184 will always be looking at screen 112. However a reason for an unduly long pause may be that rescuer 184 has become distracted with other activities of the rescue session, in which case he is not necessarily looking at screen 112, and therefore an audible alarm may be required in addition to what may be shown in screen 112.

Figure 2:
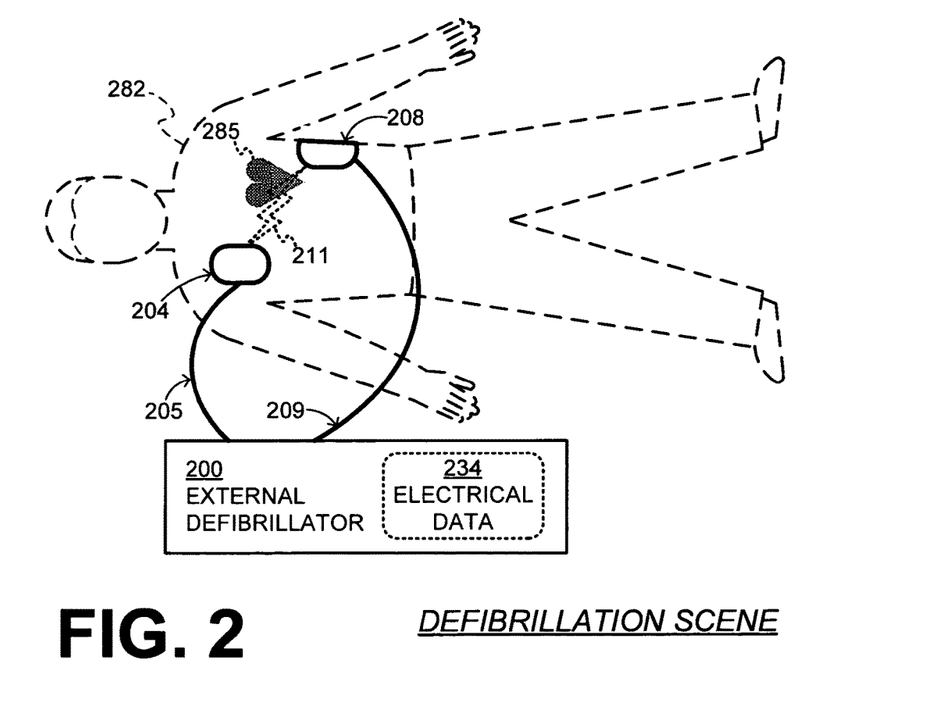
FIG. 2 is a diagram of a scene where a defibrillator is applied to the chest of a patient, and is storing patient electrical data according to embodiments.

FIG. 2 is a diagram of a defibrillation scene. A patient 283 is lying on their back. Patient 282 could be a patient in a hospital, or someone found unconscious, and then turned to be on their back. Patient 282 is experiencing a condition in their heart 285, which could be Ventricular Fibrillation (VF).

A portable external defibrillator 200 has been brought close to patient 282. Defibrillator 200 may incorporate system 100 of FIG. 1, or not. At least two defibrillation electrodes 204, 208 are usually provided with external defibrillator 200, and are sometimes called electrodes 204, 208. Electrodes 204, 208 are coupled with external defibrillator 200 via respective electrode leads 205, 209. A rescuer (not shown) has attached electrodes 204, 208 to the skin of patient 282. Defibrillator 200 can administer, via electrodes 204, 208, a brief, strong electric pulse 211 through the body of patient 282. Pulse 211, also known as a defibrillation shock, goes also through heart 285, in an attempt to restart it, for saving the life of patient 282.

Defibrillator 200 can be one of different types, each with different sets of features and capabilities. It could be a monitor defibrillator, because it is typically formed as a single unit in combination with a patient monitor. Or it could be an Automated External Defibrillator (AED).

Defibrillator 200 is capable of detecting electrical parameters of patient 282, and storing them as electrical data 234 of patient 282. Electrical data 234 may Include ECG (electrocardiogram) data, or data about the impedance of the patient, as measured between electrodes 204, 208.

At least impedance data can be converted to data derived from a session of CPR chest compressions. This is possible because, when a patient's chest is compressed, their impedance changes accordingly.

Figure 3:
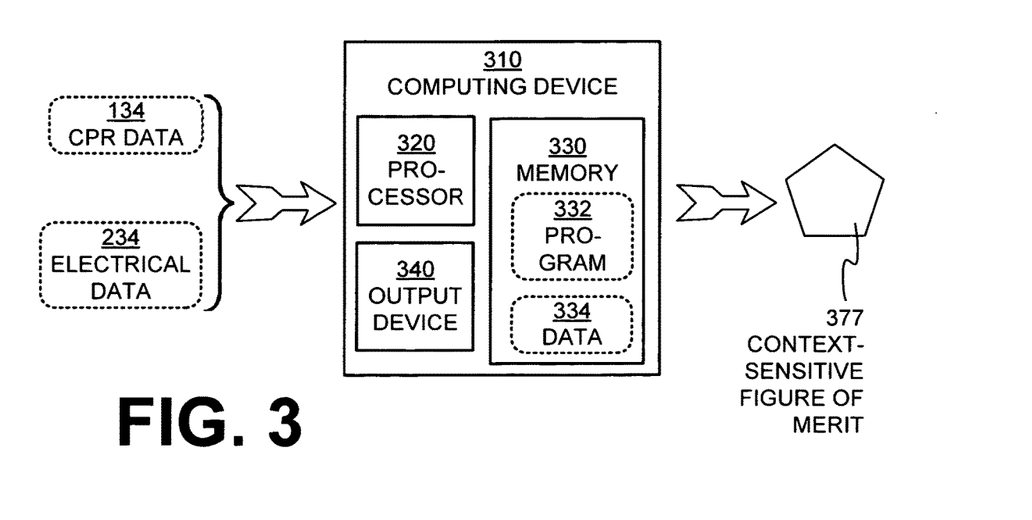
FIG. 3 is a diagram of a computing device configured according to embodiments.

FIG. 3 is a diagram of a computing device 310 configured according to embodiments. Computing device 310 may be a general purpose computer, or a module within a host system such as system 100, or within an external defibrillator such as external defibrillator 200. Examples and details can be found in the incorporated U.S. Pat. No. 8,060,199 B2.

Computing device 310 includes a processor 320. Processor 320 is configured to input patient data that is derived from a session of administering CPR chest compressions to a patient. An example of such data is CPR data 134. Such data may be acquired directly or derived from electrical data 234 as mentioned above. Processor 320 is further configured to compute a FOM 377 from the inputted patient data. It will be appreciated that FOM 377 is context sensitive, according to embodiments.

Computing device 310 also includes one or more non-transitory storage media. Such media include but are not limited to volatile memory, non-volatile memory (NVM), read only memory (ROM); random access memory (RAM); magnetic disk storage media; optical storage media; smart cards, flash memory devices, etc. in the example of FIG. 3, the non-transitory storage medium is a memory 330. These storage media, individually or in combination with others, can have stored thereon data such as data 334. Data 334 can be the inputted patient data, interim computation data, and so on. These storage media can have also stored thereon one or more programs, such as program 332. The programs can include instructions in the form of code, which processor 320 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods.

Computing device 310 additionally includes an output device 340. Output device 340 may be an output port that communicates a value of FOM 377. The value may be received and displayed by a screen, in post-event review analysis. Or, if computing device 310 is part of a system such as system 100, output device 340 can communicate the value of FOM 377, which can in turn communicate it to the rescuer via the user interface.

Embodiments of computations of figure of merit 377 are now described in more detail. These computations are made relative to the patient data. An example is now described.

Figure 4:
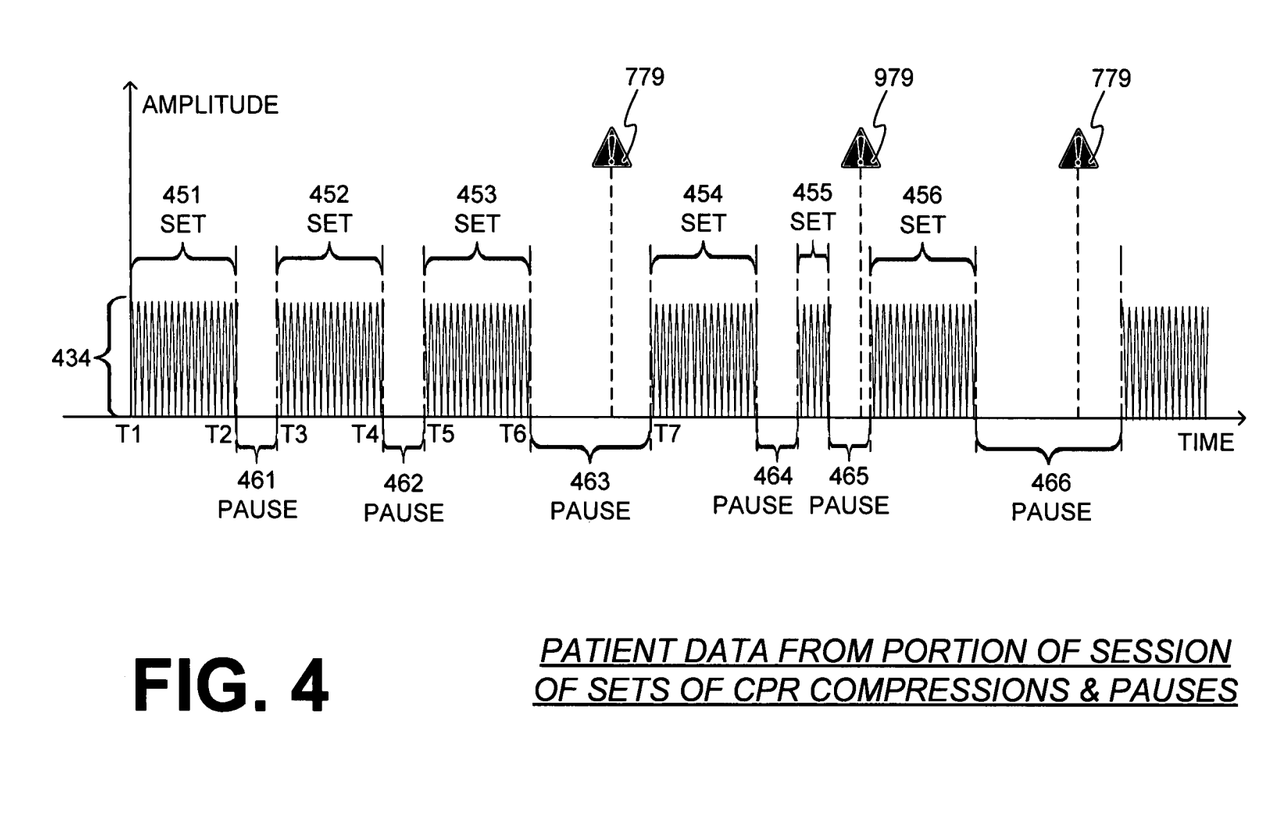
FIG. 4 is a time diagram of patient data which are derived from a portion of a session of CPR chest compressions.

FIG. 4 is a time diagram of patient data 434, which can be derived from a portion of a session of CPR chest compressions. More particularly, data 434 is data of a time displacement of the patient's chest, as he is receiving CPR chest compressions. Since data 434 denotes compression depth, it alternately be measured downward from zero, not upwards as in FIG. 4, but that does not make any difference for this description. Plus, data 434 are not from the entire session; rather, a convenient starting time T1 has been chosen on the time axis in this example only, while other starting times may be chosen, even before time T1.

Moreover, data 434 have been parsed into sets 451, 452, . . . , 456 of CPR chest compressions. Within each of the sets there are compressions and releases of the patient chest, which alternate rather quickly. It will be observed that the first few sets start and stop at times T1, T2, . . . , T7. More such times could be shown but are not, so as to not unnecessarily clutter FIG. 4. These times can be used to measure the duration of sets 451, 452, . . . , 456, and can be used in the computation of the figure of merit.

In addition, it will be observed that sets 451, 452, . . . , 456 are separated by pauses 461, 463, 463, 464, 465. A pause 466 follows set 456. Those pauses take place when rescuer 184 might interrupt administering chest compressions, so as to administer ventilations or perform other activities of the rescue effort. For purposes of this document, the releases from the chest compressions that are within one of the sets are not considered to be pauses. The time durations of pauses 461, 462, . . . , 466 an also be measured on the time axis, and can be used in the computation of the figure of merit. FIG. 4 also shows emitted alarms 779, 979 during some of the pauses, which will be described later in this document.

It will be appreciated that embodiments may be practiced after the fact, in the context of a post-event review. In such cases, the FOM can be computed using all the patient data of the session. Other embodiments may be practiced without using all the patient data of the session. For example, the FOM can be computed at least once during the rescue session, and shown to rescuer 184 using screen 112. In a real-time-display embodiment, the FOM can serve as a "pause tolerability index", reflecting how tolerant the patient's physiology is estimated to be to a reasonable-duration pause starting at that instant in time. In such an embodiment, the FOM could be derived either by 1) using the entire recording, from the beginning of data until that point in time, equally weighted across that interval, or 2) weighting recent history more strongly, and/or only deriving the measurement from a recent time interval, such as the most recent 2 (or 5, etc.) minutes. An example is now described, which does not use all the patient data of the session.

Figure 5:
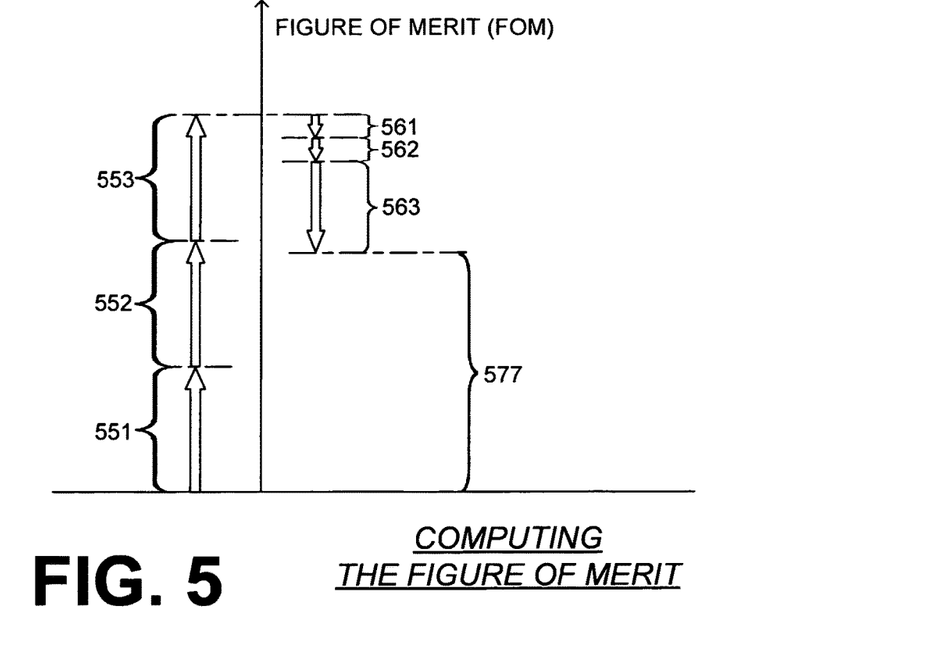
FIG. 5 is a diagram illustrating graphically components for computing a figure of merit (FOM) from some of the data of FIG. 4 according to embodiments.

FIG. 5 is a diagram illustrating graphically components for computing a figure of merit (FOM) from only some of the data of FIG. 4 according to embodiments. The FOM is computed on the vertical axis. The first three sets 451, 452, 453 contribute three respective components 551, 552, 553, which increase the value of the FOM. The first three pauses 461, 462, 463 contribute three respective penalties 561, 562, 563 that decrease the value of the FOM. The remaining difference is value 577 of the FOM.

Optionally, the FOM can be expressed as a fraction. The fraction can be with respect to unity, for example with "1.0" being a perfect score. Alternately, the FOM can be expressed as a percentage with respect to unity, with "100%" being the perfect score.

While FIG. 5 provides an aggregate result, its individual components may still be used for more detailed analysis. For example, a pauses table can be accumulated for each pause, showing its start time, end time, duration, and penalty value at the end of the duration. During post event review, the pauses table can be reviewed, with its entries sorted by any variable, such as the penalty values from highest to lowest.

In some embodiments, a patient record can be created from the patient data, to which other elements can be added, for example by being superimposed. An image of such a patient record could be the patient data of FIG. 4, to which alarms have been superimposed, as will be described later in this document. Other elements that can be superimposed are data about any one of the pauses and the value of its respective penalty. Or it can be all the pauses. In some embodiments, a reviewer afterwards can click through the pauses hierarchically, based on the penalty values.

Figure 6:
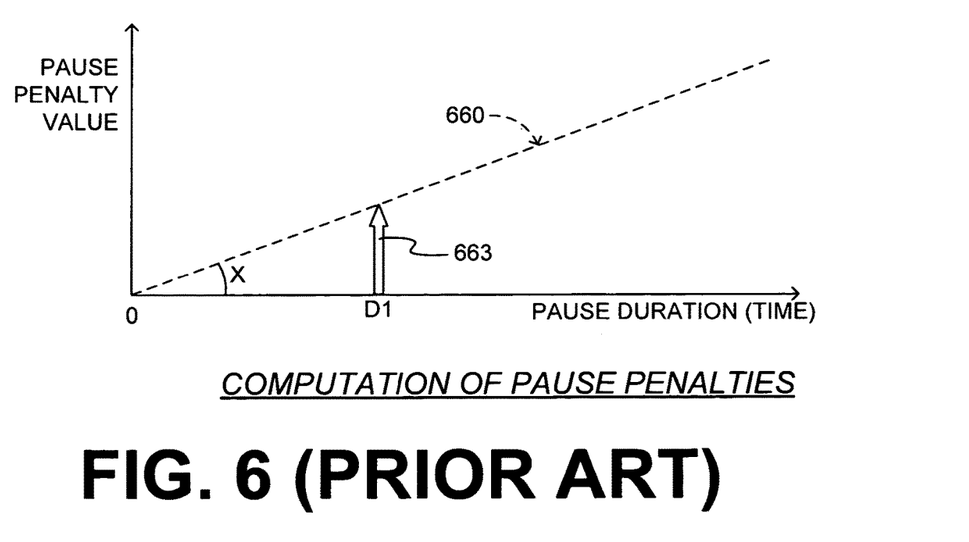
FIG. 6 is a diagram showing how a FOM penalized for pauses in the prior art.

FIG. 6 is a diagram showing how a figure of merit is penalized for pauses in the prior art. In other words, it shows the computation of penalties due to pauses, such as penalties 561, 562, 563. In FIG. 6, the pause penalty value is plotted against a duration of the pause in units of time. The relationship is linear, denoted by a straight line 660. The relationship is also constant, as line 660 has a fixed slope, which would be the tangent of angle X. For a duration D1, the penalty has the value of arrow 663, which starts from the horizontal time axis and reaches up to line 660. In other words, penalty 663 has a value determined from a constant linear dependence 660 on a duration D1 of its respective pause. Of course, arrow 663 would be inverted if it were used in the representation of FIG. 5.

There are problems with the linear relationship of FIG. 6. First, while a single unduly long pause can have a harmful effect on a patent, its unduly long duration can obscured if it is added to and averaged with other short pauses. Second, not all pauses have the same effect of the patient. For example, some pauses that start after an unduly short set of CPR compressions are more harmful to the patient. An example is the beginning of pause 465, after unduly short set 455.

According to embodiments, at least a certain one of the pauses can contribute a penalty to the FOM. The penalty can have a value determined from at least one control factor other than a constant linear dependence on the duration of the pause. It is preferred that all pauses contribute respective penalties to the FOM, and that each of the penalties has a value determined consistently with the value of the certain penalty. In some of those embodiments, all penalties are computed the same way. In some embodiments, processor 320 is further configured to compute a sum of all the penalties, and output device 340 is further configured to output also the sum.

It was mentioned above that embodiments may be practiced during the rescue session. Moreover, output device 340 or the user interface can be further configured to emit an alarm, if the value of the FOM, or of the certain penalty, or the sum of the penalties exceeds a respective threshold.

Examples of the control factor according to embodiments are now described. In addition, these individually described examples of control factors can be combined as desired. These examples are described in terms also of the certain penalty value shown on the vertical axis while the pause duration is shown in the horizontal axis. They should be contrasted to FIG. 6, which shows the pause penalty value as being determined from the constant linear dependence 660 on the duration of the pause.

Figure 7:
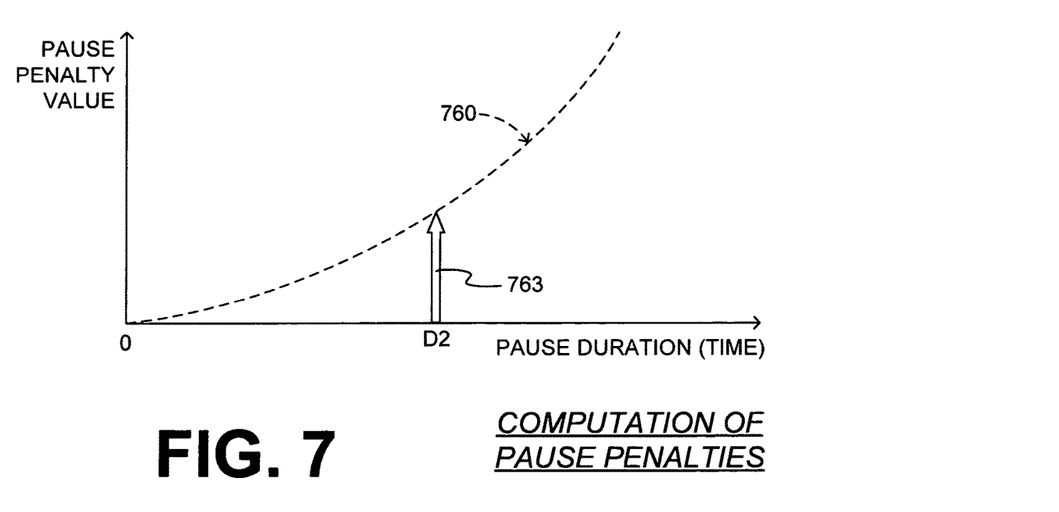
FIG. 7 is a diagram showing how a pause penalty value of a FOM is computed according to an embodiment.

FIG. 7 is a diagram showing how a pause penalty value of a figure of merit is computed according to an embodiment. In this embodiment, the control factor includes a nonlinear increase 760 of the certain penalty value with the pause duration, for at least a range of possible values of the duration. For example, at duration D2, the penalty value is represented by the length of arrow 763. Plus, in a range of values around D2, the certain penalty value changes non-linearly with the duration.

An advantage of the non-linearly increasing penalty value is that unduly longer pauses can become penalized disproportionately, as desired. Plus, a nonlinear increase such as increase 760 might be responsible for causing an alarm 779 to be emitted. Alarm 779 is shown in FIG. 4, superimposed over the patient data, during pauses 463, 466. Upon perceiving emitted alarm 779, rescuer 184 reprioritize doing compressions.

Figure 8:
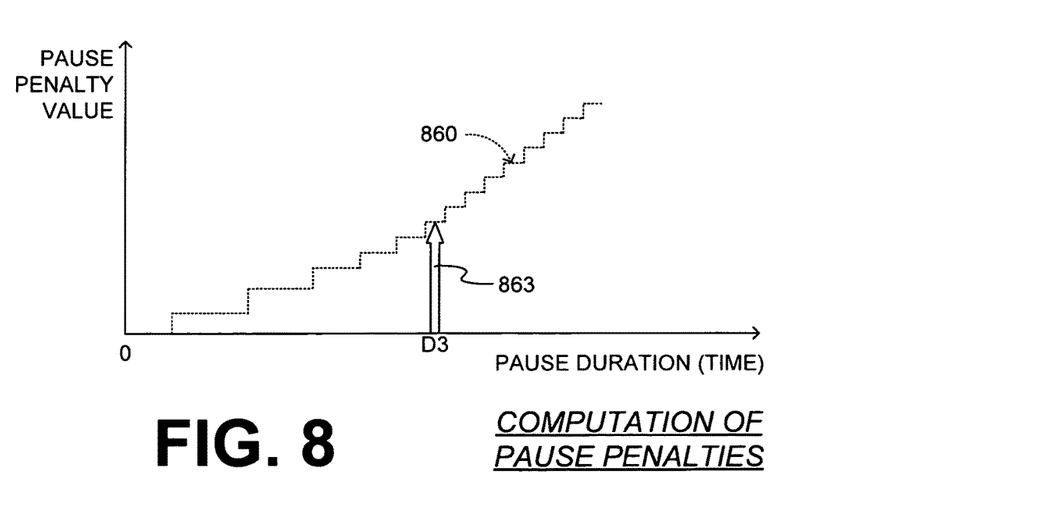
FIG. 8 is a diagram showing how a pause penalty value of a FOM is computed according to another embodiment.

FIG. 8 is a diagram showing how a pause penalty value of a figure of merit is computed according to another embodiment. In this embodiment, the control factor includes a staircase-type increase no of the certain penalty value with the pause duration, for at least a range of possible values of the duration—here the entire shown range. For example, at duration D3, the penalty value is represented by the length of arrow 863. It will be recognized that the specific staircase-type increase 860 also increases non-linearly at higher values, although that is not necessary for practicing the invention.

Figure 9:
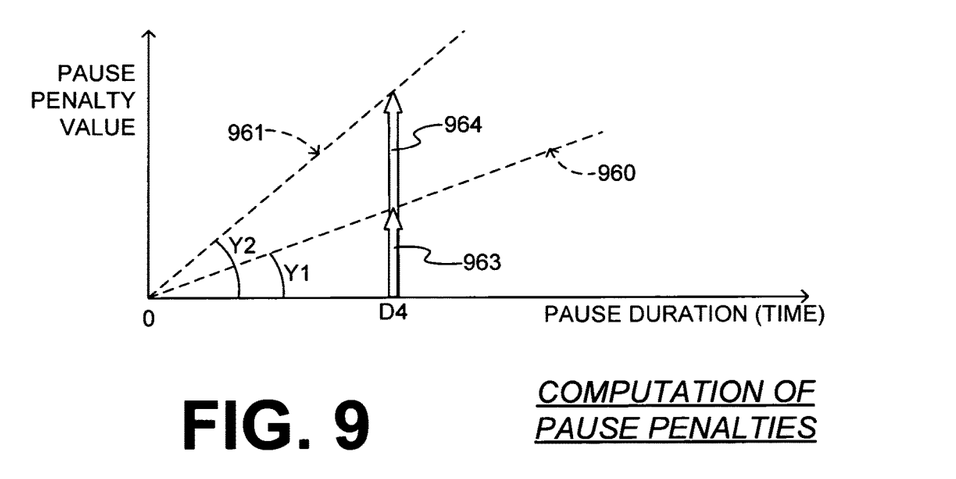
FIG. 9 is a diagram showing how a pause penalty value of a FOM is computed according to an additional embodiment.

FIG. 9 is a diagram showing how a pause penalty value of a figure of merit is computed, according to an additional embodiment. In this embodiment, the control factor includes a different rate of increase of the certain penalty value with the duration, depending on a condition. Two possible rates 960, 961 are shown. Rates 960, 961 are linear, but that is for example only, and they could have different shapes. Rate 960 has a slope given by the tangent of angle Y1, while rate 961 has a slope given by the tangent of angle Y2. Rate 961 is steeper, and accumulates penalty value faster. For example, at duration D4, if rate 960 is applied, the penalty value is represented by the length of arrow 963. However, if steeper rate 961 is applied, the penalty value is represented by the length of larger arrow 964.

Accordingly, the penalty value can be accumulated faster, depending on a condition. There can be any number of possible conditions.

In one embodiment, the condition may include the duration of a set of chest compressions prior to the pause; if that is too short, then the pause cannot afford to be too long. For example, a steep increase such as increase 961 might be responsible for causing an alarm 979 to be emitted. Alarm 979 is shown in FIG. 4, superimposed over the patient data, during pause 465. Pause 465 is not itself long, but takes place after an unduly short set 455. Upon perceiving emitted alarm 979 rescuer 184 reprioritized doing compressions.

In another embodiment, the condition may include a ratio of a total duration of pauses to a total duration of chest compressions for a preceding time interval, such as the preceding three minutes, or the ventilation rate within the preceding interval of interest, such as 30 sec. In an additional embodiment, the condition may include proximity to the beginning of the recording, i.e. to the portion of the session that is known, to an event of significance, such as defibrillation shock beginning of mechanical CPR, user-identified time of collapse, and so on.

In one more embodiment, a present characterization can be input of a cardiac rhythm of the patient whose data is being used, to take into account how well the patient is doing. Then the condition may include the present characterization of the cardiac rhythm. For example, the penalty value can be accumulated at different speeds, depending on whether the characterization is "shockable", "brady/PEA/asystole" or "ROSC-like", where PEA stands for Pulseless Electrical Activity, and ROSC stands for Return of Spontaneous Circulation.

Figure 10:
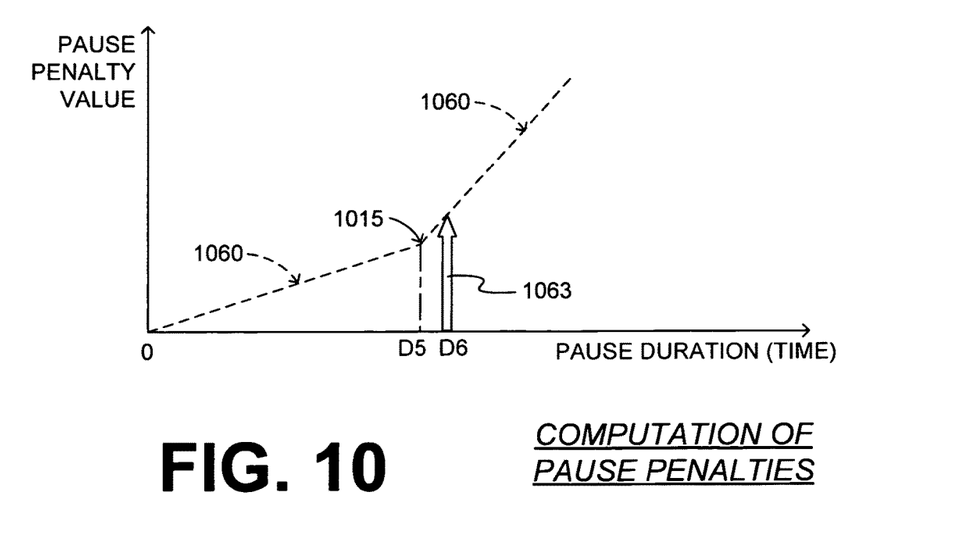
FIG. 10 is a diagram showing how a pause penalty value of a FOM is computed according to a further embodiment.

FIG. 10 is a diagram showing how a pause penalty value of a figure of merit is computed according to a further embodiment. In this embodiment, line 1060 has an inflection point 1015 at a cross-over duration D5. The value of the penalty has a constant linear dependence on the duration for values of the duration up to cross-over duration D5. And the control factor includes a linear increase of the penalty value with the duration for values of the duration larger than the cross-over duration, in which the linear increase has a second rate different than the constant linear dependence. For example, at duration D6, the penalty value is represented by the length of arrow 1063.

If a physiology model is computed, in whole or in part, the above-described embodiments might be refined.

The above-mentioned devices and/or systems perform functions, processes and/or methods, as described in this document. Moreover, processes, methods and algorithms are described below. These processes, methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary however, and there may be cases where modules are equivalently aggregated into a single program, even with unclear boundaries. In some instances, software is combined with hardware, in a mix called firmware.

This detailed description also includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 11:
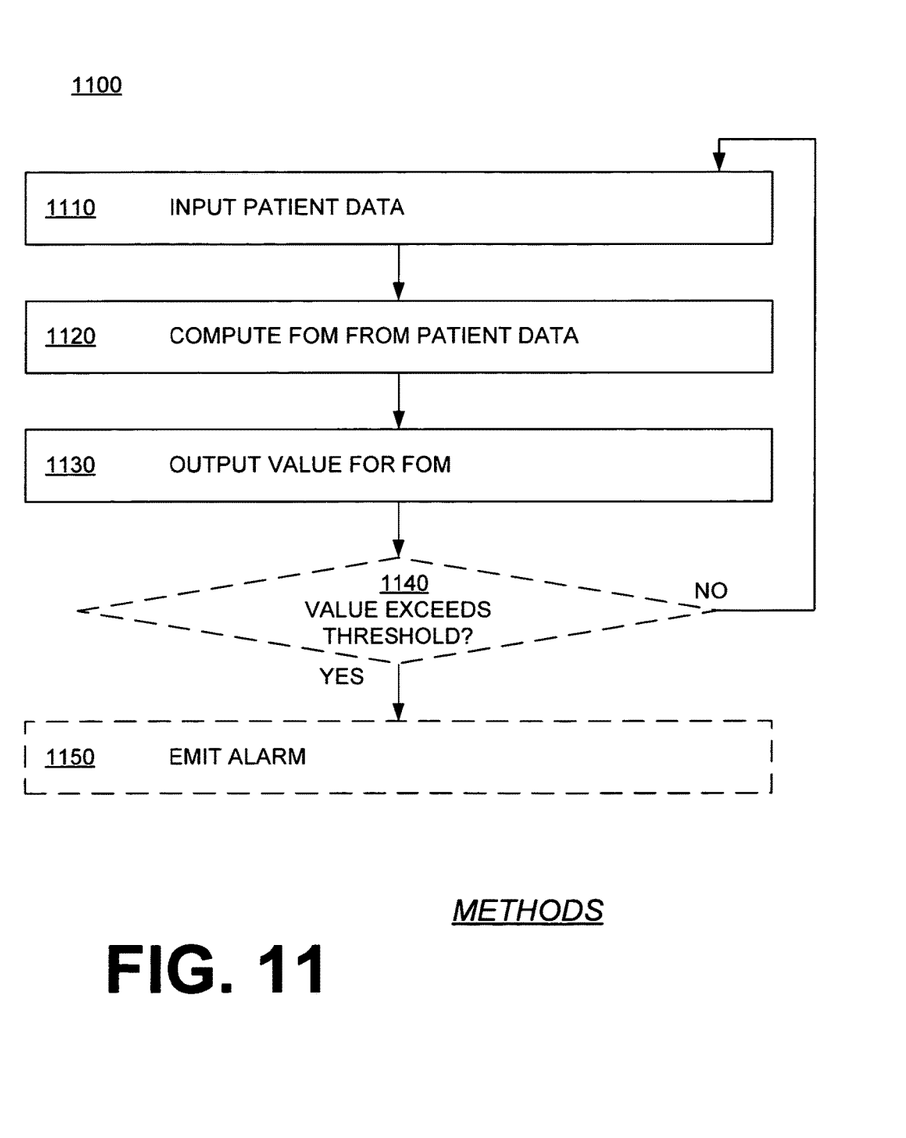
FIG. 11 is a flowchart for illustrating methods according to embodiments.

FIG. 11 shows a flowchart 1100 for describing methods according to embodiments. The methods of flowchart 1100 may also be practiced by embodiments described above, and with the ways and variations described above.

According to an operation 1110, patient data is input. The patient data may be derived from a session of administering to patient 182 sets of CPR chest compressions that are separated by pauses. According to another operation 1120, a figure of merit (FOM) is computed from the patient data. According to one more operation 1130, a value for the FOM is output.

According to another, optional operation 1140, it is inquired whether a value exceeds a threshold. The value can be that of the FOM, or of a penalty, or of a sum of the penalties computed at operation 1120. If so, then according to another optional operation 1150, an alarm is emitted. If not, execution returns to operation 1110.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced. Indeed, examples or embodiments of the invent or may be practiced according to what is described, or yet differently, and also in conjunction with other present or future technologies.

Reference to any prior art in this specification is not, and should not be taken as, an acknowledgement or any form of suggestion that this prior art forms parts of the common general knowledge in any country.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A computing device for providing Cardiopulmonary Resuscitation (CPR) feedback to a rescuer who is performing on a patient sets of chest compressions that are separated by pauses, the computing device comprising:
    a processor configured to:
        receive patient CPR data, the patient CPR data including at least one of patient electrocardiogram (ECG) data, from one or more ECG sensors, and patient transthoracic impedance data, from one or more patient impedance sensors, the patient CPR data indicative of at least a portion of a CPR session during which a plurality of CPR chest compressions sets are administered, each of the plurality of chest compressions sets separated by at least a pause having a duration;
        identifying, from the received patient CPR data, two or more CPR compression sets and one or more pauses separating the two or more CPR compression sets;
        calculating the duration for each of the one or more pauses;
        determine a figure of merit (FOM) for the at least a portion of the CPR session, the FOM including an aggregate of one or more compression values and one or more penalty values, each compression value associated with at least one of the two or more identified CPR compressions sets of the CPR session and increasing the FOM and each penalty value associated with at least a pause of the CPR session and decreasing the FOM, the penalty value for each pause;
        computing a penalty value for each pause based at least in part on at least one control factor, the control factor including a first control factor that applies a penalty value to the FOM for each pause based on a pre-determined non-linear relationship between the penalty value and the duration of the pause;
        generate rescuer feedback based on a comparison of the determined FOM with a threshold FOM, the rescuer feedback including at least an alteration to the administration of chest compressions when the determined FOM exceeds the threshold FOM; and
    an output device configured to output at least one of the FOM and the generated rescuer feedback, the rescuer feedback including the alteration to the administration of chest compressions and a prompt to the rescuer to alter the administration of chest compressions on the patient.

2. The computing device of claim 1, in which the processor is further configured to create a patient record from the patient CPR data, the patient records also including data about the at least a pause and the penalty value.

3. The computing device of claim 1, in which the FOM is computed using all the patient CPR data of the CPR session.

4. The computing device of claim 1, in which the FOM is computed at least once without using all the patient CPR data of the CPR session.

5. The computing device of claim 1, in which the output device is further configured to emit an alarm, if the one or more penalty values exceeds a respective penalty threshold.

6. The computing device of claim 1, in which the FOM is expressed as one of a fraction and a percentage with respect to unity.

7. The computing device of claim 1, in which each pause of the CPR session contributes respective penalty values to the FOM, and
    each of the penalty values has a value determined consistently with the one or more penalty values.

8. The computing device of claim 7, in which the processor is further configured to: compute a sum of all the penalty values, and
    the output device is further configured to output the sum.

9. The computing device of claim 8, in which the output device is further configured to emit an alarm, if the sum exceeds a sum threshold.

10. The computing device of claim 1, in which the first control factor includes a nonlinear increase of the penalty value with the duration of the pause for at least a range of possible values of the duration of the pause.

11. The computing device of claim 1, in which the first control factor includes a staircase-type increase of the penalty value with the duration of the pause for at least a range of possible values of the duration of the pause.

12. The computing device of claim 1, in which the first control factor includes a different rate of increase of the penalty value with the duration of the pause depending on a condition.

13. The computing device of claim 12, in which
    the condition includes a duration of a chest compression set prior to the pause.

14. The computing device of claim 12, in which the condition includes a ratio of a total duration of pauses to a total duration of chest compression sets for a preceding time interval.

15. The computing device of claim 12, in which the processor is further configured to receive a present characterization of a cardiac rhythm, and
the condition includes the present characterization of the cardiac rhythm.

16. The computing device of claim 1, in which the penalty value has a constant linear dependence on the duration of the pause for values of the duration up to a cross-over duration of an inflection point, and
the at least a control factor includes a linear increase of the penalty value with the duration of the pause for values of the duration larger than the cross-over duration, in which the linear increase has a second rate different than the constant linear dependence.

17. The device of claim 1, in which the at least a control factor includes that the penalty value increases at a first instantaneous rate when the duration of the pause has a first value and that the penalty value increases at a second instantaneous rate different from the first instantaneous rate when the pause duration has a second value different from the first value.

18. A computing device for providing Cardiopulmonary Resuscitation (CPR) feedback to a rescuer who is performing on a patient sets of chest compressions that are separated by pauses, the computing device comprising: a processor configured to: receive patient CPR data indicative of a least a portion of a CPR session during which two or more CPR compression sets were administered, the patient CPR data received from at least one of an electrocardiogram (ECG) sensor or a transthoracic impedance sensor, and including at least one of patient ECG data or patient transthoracic impedance data; parse, from the received patient data, at least two or more CPR compression sets and one or more pauses separating the two or more CPR compression sets, based on the at least one of the patient ECG data or the patient transthoracic impedance data; determine a duration of each of the one or more pauses based on at least one of the parsing of the two or more CPR compression sets or the parsing of the one or more pauses; compute a penalty value for each of the one or more pauses based at least in part on one or more control factors, the one or more control factors including a first control factor that calculates a penalty value to each of the one or more pauses based on a pre-determined non-linear relationship between the penalty value and the duration of the one or more pauses; determine a compression value for each of the two or more CPR compression sets; generate a figure of merit (FOM) for the at least of a CPR session, the FOM an aggregate of the penalty value for each of the one or more pauses and the compression value for each of the two or more CPR compression sets, each of the penalty values decreasing the FOM by the penalty value and each of the compression values increasing the FOM by the compression value; and generate and transmit rescuer feedback to the rescuer based on a comparison of the determined FOM with a threshold FOM, the rescuer feedback including at least an alteration to the administration of chest compressions.

* * * * *